US010820911B2

(12) United States Patent
Delman et al.

(10) Patent No.: US 10,820,911 B2
(45) Date of Patent: Nov. 3, 2020

(54) SELF-PROPELLING SURGICAL DEVICE

(71) Applicant: Peninsula Surgical Solutions, LLC, San Pedro, CA (US)

(72) Inventors: Allan Michael Delman, San Pedro, CA (US); Freidoon Rastegar, San Pedro, CA (US); Connor Delman, Sacramento, CA (US)

(73) Assignee: Peninsula Surgical Solutions, LLC, San Pedro, CA (US)

( * ) Notice: Subject to any disclaimer, the term of this patent is extended or adjusted under 35 U.S.C. 154(b) by 0 days.

(21) Appl. No.: 16/514,896

(22) Filed: Jul. 17, 2019

(65) Prior Publication Data
US 2020/0100799 A1    Apr. 2, 2020

Related U.S. Application Data

(60) Provisional application No. 62/672,915, filed on May 17, 2018.

(51) Int. Cl.
*A61B 17/16* (2006.01)
*A61B 17/88* (2006.01)
*A61B 17/00* (2006.01)

(52) U.S. Cl.
CPC ........ *A61B 17/1624* (2013.01); *A61B 17/162* (2013.01); *A61B 17/1615* (2013.01); *A61B 17/1626* (2013.01); *A61B 17/1628* (2013.01); *A61B 17/8875* (2013.01); *A61B 2017/00022* (2013.01); *A61B 2017/00057* (2013.01); *A61B 2017/00075* (2013.01); *A61B 2017/00199* (2013.01); *A61B 2017/00398* (2013.01); *A61B 2017/00477* (2013.01); *A61B 2017/00734* (2013.01)

(58) Field of Classification Search
CPC ......... A61B 17/1615–17/1624; Y10S 408/712
See application file for complete search history.

(56) References Cited

U.S. PATENT DOCUMENTS

| | | | | |
|---|---|---|---|---|
| 3,421,351 A | * | 1/1969 | Doran | B21D 11/14 72/64 |
| 3,570,606 A | * | 3/1971 | Guritz | B25H 1/0021 173/186 |
| 4,358,888 A | * | 11/1982 | Zankl | B23Q 3/15526 29/26 A |
| 4,404,727 A | | 9/1983 | Zankl | |
| 5,833,404 A | * | 11/1998 | Johnson | B23Q 5/265 408/130 |
| 5,885,036 A | * | 3/1999 | Wheeler | B23Q 9/0028 408/1 R |
| 8,894,654 B2 | | 11/2014 | Anderson | |
| 2009/0245956 A1 | * | 10/2009 | Apkarian | A61B 17/1626 408/1 R |

(Continued)

FOREIGN PATENT DOCUMENTS

CN    107997817 A    5/2018

*Primary Examiner* — Zade Coley
(74) *Attorney, Agent, or Firm* — Seed IP Law Group LLP

(57) ABSTRACT

The present disclosure is directed to a self-propelling surgical device and method for using the same. The device is configured to drill a hole into an object, such as a bone, and subsequently insert an implant, such as a screw or pin, into the hole. The device drills the hole and inserts the implant under its own power. The device may perform desired actions automatically or manually.

20 Claims, 8 Drawing Sheets

(56) References Cited

U.S. PATENT DOCUMENTS

| | | | |
|---|---|---|---|
| 2009/0326537 A1* | 12/2009 | Anderson | A61B 90/06 606/80 |
| 2010/0331852 A1 | 12/2010 | Neubardt | |
| 2011/0245833 A1* | 10/2011 | Anderson | B25B 23/0064 606/80 |
| 2016/0067006 A1 | 3/2016 | Steinberg | |
| 2017/0245868 A1 | 8/2017 | McGinley et al. | |
| 2018/0000526 A1* | 1/2018 | O'Neil | A61B 90/39 |
| 2018/0325528 A1 | 11/2018 | Windolf et al. | |

* cited by examiner

SELF-PROPELLING SURGICAL DEVICE

BACKGROUND

Technical Field

The present disclosure is directed to a medical device and method for using the same.

Description of the Related Art

Orthopedic surgeons treat musculoskeletal system ailments, such as injuries to bones, joints and ligaments. This may require the insertion of an implant, such as a screw or pin, into bone. Generally, the implant is inserted into the bone by drilling a hole into the bone with a drill bit, removing the drill bit from the hole, measuring the depth of the hole with a depth gauge, inserting the implant into the hole with a screw driver, and repeating this process for each implant. This process has several drawbacks. One drawback is that the orthopedic surgeon uses physical force to push the drill while driving the drill bit into the bone. Similarly, manual force is used to withdraw the drill bit and to insert the screw into the hole with a screwdriver. These actions, which are often done repetitively, are fatiguing. Furthermore drilling a hole in bone often requires substantial force and may result in the inadvertent passage of the drill too far, potentially injuring the patient by penetrating the soft tissue. In addition, the surgeon may mistakenly insert the screw into the hole at the wrong angle and/or alignment impairing the strength or effectiveness of the implant. Another drawback is that it is often difficult for the surgeon to obtain an accurate measurement of depth using the depth gauge because it requires tactile feedback, which can be demanding in the clinical setting. If the depth measurement is inaccurate, the surgeon may insert a screw of the wrong length, which should then be removed and discarded, resulting in wasted hardware and increased costs. In addition, if the depth measurement is inaccurate or technically difficult, verification may require repeated radiographs, which is time consuming. As a result, patients are subjected to longer anesthesia times and there is greater radiation exposure to the patient, the surgeon and the ancillary medical staff.

BRIEF SUMMARY

The present disclosure is directed to a self-propelling surgical device and method for using the same. The device is configured to drill a hole into an object, such as a bone; determine a depth of the hole; select an implant, such as a screw or pin, to be inserted into the hole; and insert the implant into the hole. The device drills the hole and inserts the implant without physical intervention on part of a user. More specifically, in contrast to traditional drills and screw drivers, the user does not apply a physical force to the device to drill the hole or insert the implant. Rather, the device drills the hole and inserts the implant under its own power. In addition, the user does not move the device when switching between drilling the hole to inserting the implant. Instead, the device remains stationary during both of the drilling of the hole and the inserting of the implant.

BRIEF DESCRIPTION OF THE SEVERAL VIEWS OF THE DRAWINGS

In the drawings, identical reference numbers identify similar features or elements. The size and relative positions of features in the drawings are not necessarily drawn to scale.

DETAILED DESCRIPTION

In the following description, certain specific details are set forth in order to provide a thorough understanding of various aspects of the disclosed subject matter. However, the disclosed subject matter may be practiced without these specific details. In some instances, well-known structures and methods of using devices, such as drills, screw drivers, and sensors, have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

The present disclosure is directed to a self-propelling surgical device and method for using the same.

Figure 1:
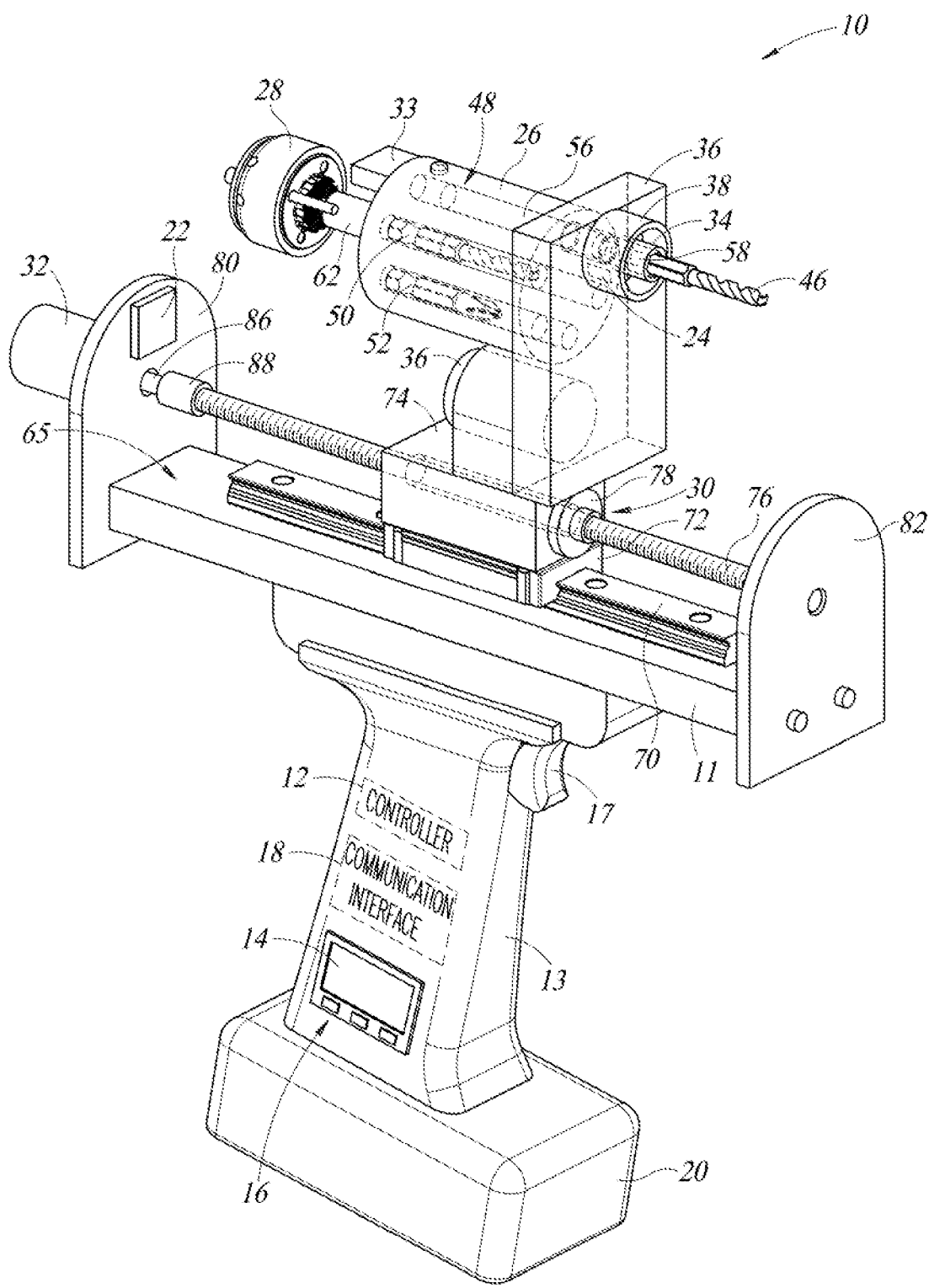
FIG. 1 is an angled view of a self-propelling device according to an embodiment of the present disclosure.
Figure 2:
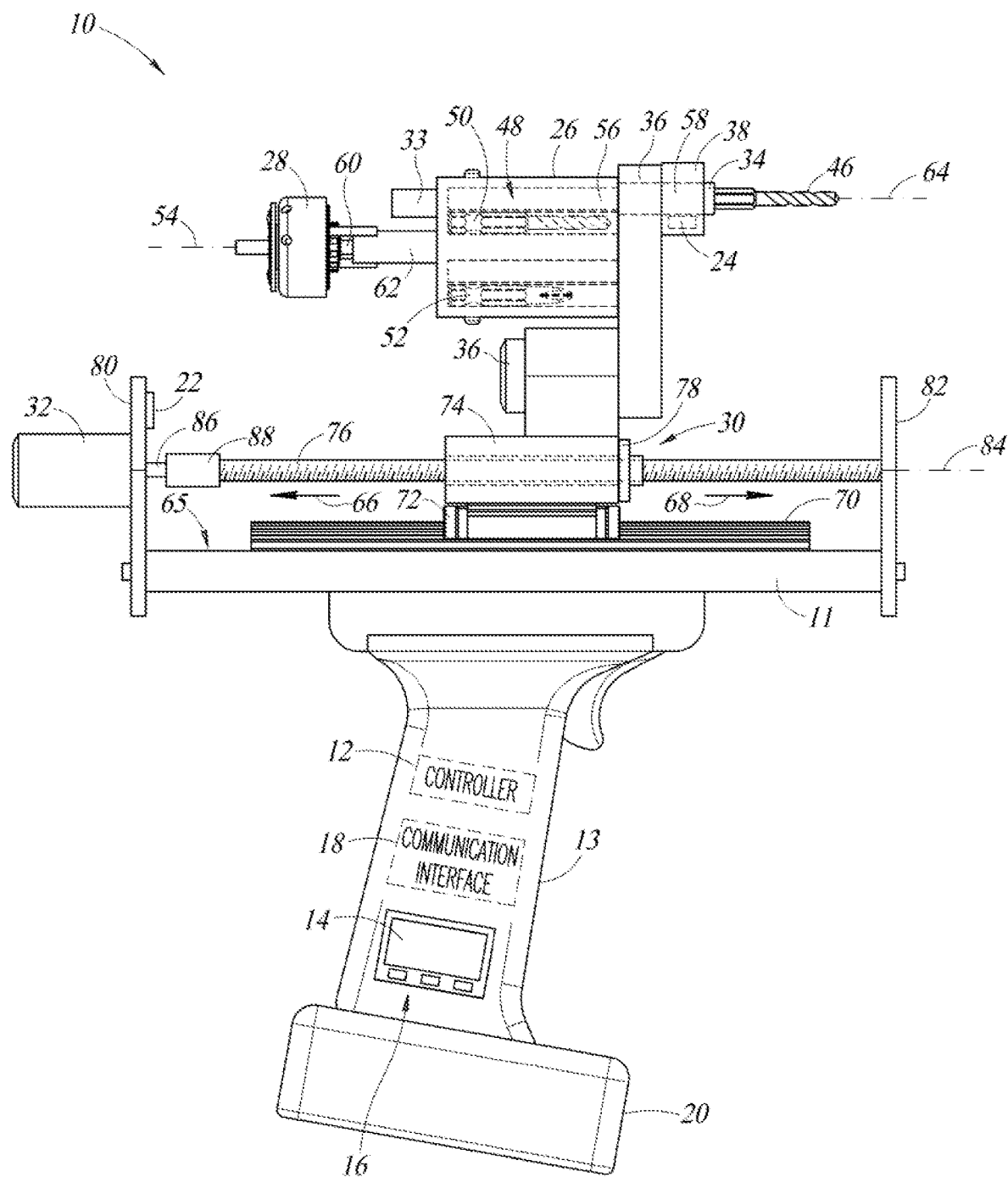
FIG. 2 is a side view of the device of FIG. 1.

FIG. 1 is an angled view of a self-propelling device 10 according to an embodiment of the present disclosure. FIG. 2 is a side view of the self-propelling device 10. It is beneficial to review FIGS. 1 and 2 together.

The device 10 includes a frame 11, a handle 13, a controller 12, a display 14, an input interface 16, a trigger 17, a communication interface 18, a power source 20, a distance sensor 22, a force sensor 24, a rotating cylinder 26, a rotating cylinder actuator 28, a bit loader 33, a bit mount 34, a motor 36, a torque limiter 38, a rail system 30, and a rail system actuator 32.

The frame 11 provides a support for the various components of the device 10. As will be discussed in further detail below, the distance sensor 22, the force sensor 24, the rotating cylinder 26, the rotating cylinder actuator 28, the bit loader 33, the bit mount 34, the motor 36, the torque limiter 38, the rail system 30, and the rail system actuator 32 are positioned on the frame 11. In one embodiment, the frame 11 is made of a rigid material, such as metal or plastic.

The handle 13 is coupled to the frame 11. The handle 13 allows the user to hold and handle the device 10 with a single hand or with two hands. As will be discussed in further detail below, the handle 13 houses various components of the device 10. For example, in one embodiment, one or more of the controller 12, the display 14, the input interface 16, the communication interface 18, and the power source 20 are positioned on the handle 13. In one embodiment, the handle 13 is made of a rigid material, such as metal or plastic.

The controller 12 controls the overall operation of the device 10. Namely, the controller 12 controls and coordinates the operation of the display 14, the communication interface 18, the distance sensor 22, the force sensor 24, the rotating cylinder actuator 28, the rail system actuator 32, and the motor 36. For example, in one or more embodiments, the controller 12 instructs the display 14 to display various information, instructs the communication interface 18 to transmit and receive data from a server, instructs the distance sensor 22 and the force sensor 24 to obtain measurements, activates the rotating cylinder actuator 28 to rotate the rotating cylinder 26, activates the rail system actuator 32 to move the rail system 30, and activates the motor 36 to rotate the bit mount 34. Operation of the controller 12 will be discussed in further detail below.

The controller 12 may be any type of controller, processor, or application specific integrated circuit (ASIC). In addition, the controller 12 may include or be coupled to memory for storing various types of data.

The controller 12 may be located anywhere on the device 10. In one embodiment, as shown in FIGS. 1 and 2, the controller 12 is located within the handle 13 of the device 10. In one embodiment, the controller 12 is located on the frame 11.

The display 14 displays information to the user. The information includes various types of data and parameters related to the device 10 and processes performed by the device 10. In one embodiment, the display 14 displays a target location (e.g., femur, knee, spine, tibia, etc.) of a drill and/or implantation process performed by the device 10. In one embodiment, the display 14 displays a current speed of the rotating cylinder actuator 28, the rail system actuator 32, and/or the motor 36. In one embodiment, the display 14 displays a size and/or type of an implant (e.g., the diameter or length of a screw or pin) to be used. In one embodiment, the display 14 displays safety information (e.g., maximum size of an implant that may be used, maximum depth of a hole that can be drilled into the target location, etc.). In one embodiment, the display 14 displays measurements of the distance sensor 22 and the force sensor 24. In one embodiment, the display 14 displays a current depth of a hole drilled by the device 10. In one embodiment, the display 14 displays a target depth of a hole drilled by the device 10. In one embodiment, the display 14 displays a remaining depth until a target depth of a hole drilled by the device 10 is reached. In one embodiment, the display 14 displays a power level of the power source 20. In one embodiment, the display 14 displays types of bits loaded in the rotating cylinder 26. In one embodiment, the display 14 displays a type of the bit currently loaded in the bit mount 34.

The display 14 may be any type of display, such as a digital display, light emitting diode (LED) display, organic light emitting diode (OLED) display, etc. The display 14 may be located anywhere on the device 10. In one embodiment, as shown in FIGS. 1 and 2, the display 14 is located on the handle 13 of the device 10. In one embodiment, the display 14 is located on the frame 11.

The input interface 16 is used by the user to input information into the device 10 and set parameters for the device 10, start or stop a drill process, and start or stop an implantation process. In one embodiment, the user utilizes the input interface 16 to input or set a target location (e.g., femur, knee, spine, tibia, etc.) of a drill and/or implantation process performed by the device 10. In one embodiment, the user utilizes the input interface 16 to input or set a current speed of the rotating cylinder actuator 28, the rail system actuator 32, and/or the motor 36. In one embodiment, the user utilizes the input interface 16 to input or set a size and/or type of an implant (e.g., the diameter or length of a screw or pin) to be used. In one embodiment, the user utilizes the input interface 16 to input or set safety information (e.g., maximum size of an implant that may be used, maximum depth of a hole that can be drilled into the target location, etc.). In one embodiment, the user utilizes the input interface 16 to input or set calibration data for the distance sensor 22 and/or the force sensor 24. In one embodiment, the user utilizes the input interface 16 to input or set a target depth of a hole drilled by the device 10. In one embodiment, the user utilizes the input interface 16 to input or set types of bits loaded in the rotating cylinder 26. In one embodiment, the user utilizes the input interface 16 to input or set a type of the bit currently loaded in the bit mount 34. In one embodiment, the user utilizes the input interface 16 to set the mode of insertion to either a neutralization mode or a lag mode. In one embodiment, the user utilizes the input interface 16 to input or set whether the implant is to be unicortical or bicortical. In one embodiment, the user utilizes the input interface 16 to input or set whether the device is to be used in an automatic or manual mode, which will be discussed in further detail below.

The input interface 16 may be any type of input device, such as a keyboard, a touchscreen, buttons, a dial, etc. In one embodiment, as shown in FIG. 2, the input interface 16 includes a plurality of buttons.

The input interface 16 may be located anywhere on the device 10. In one embodiment, as shown in FIG. 2, the input interface 16 is located on the handle 13 of the device 10. In one embodiment, the input interface 16 is located on the frame 11.

In one embodiment, the input interface 16 and the display 14 are separate devices. In one embodiment, the input interface 16 and the display 14 are integrated into a single device. For example, the input interface 16 and the display 14 may be a touch screen overlaying a display.

The trigger 17 is used to start and stop a drill process and an implantation process. For example, in the manual mode, a user may start a drill process by squeezing the trigger 17, and stop the drill process by releasing the trigger 17. In the automatic mode, the user may start the drill process by squeezing and releasing the trigger 17, and stop the drill process by squeezing and releasing the trigger 17 a second time. In one embodiment, as shown in FIGS. 1 and 2, the trigger 17 is positioned on the handle 13.

The communication interface 18 provides communication between the device 10 and an external device, such as a server, computer, tablet, mobile device (e.g., smart phone), and laptop. Namely, the communication interface 18 receives and transmits data from the external device.

In one embodiment, the communication interface 18 receives input information and parameters for the device 10. For example, in one or more embodiments, the communication interface 18 receives data from the external device to input or set one or more of a target location (e.g., femur, knee, spine, tibia, etc.) of a drill and/or implantation process performed by the device 10; a current speed of the rotating cylinder actuator 28, the rail system actuator 32, and/or the motor 36; a size and/or type of an implant (e.g., the diameter or length of a screw or pin) currently loaded in the device 10;

safety information (e.g., maximum size of an implant that may be used, maximum depth of a hole that can be drilled into the target location, etc.); calibration data for the distance sensor 22 and/or the force sensor 24; a target depth of a hole being drilled by the device 10; types of bits loaded in the rotating cylinder 26; and a type of the bit currently loaded in the bit mount 34.

In one embodiment, the communication interface 18 transmits status information of the device 10. For example, in one or more embodiments, the communication interface 18 transmits, to the external device, one or more of a target location (e.g., femur, knee, spine, tibia, etc.) of a drill and/or implantation process performed by the device 10; a current speed of the rotating cylinder actuator 28, the rail system actuator 32, and/or the motor 36; a size and/or type of an implant (e.g., the diameter or length of a screw or pin) currently loaded in the device 10; safety information (e.g., maximum size of an implant that may be used, maximum depth of a hole that can be drilled into the target location, etc.); current measurements of the distance sensor 22 and/or the force sensor 24; a current depth of a hole being drilled by the device 10; a target depth of a hole being drilled by the device 10; a remaining depth until a target depth of a hole being drilled by the device 10 is reached; a power level of the power source 20; types of bits loaded in the rotating cylinder 26; and a type of the bit currently loaded in the bit mount 34.

The communication interface 18 may be any type of device that transmits and receives data. The communication interface 18 may use wired or wireless communication channels. For example, the communication interface 18 may transmit and receive data using Wi-Fi, Bluetooth, an Ethernet connection, or a Universal Serial Bus (USB) connection.

The communication interface 18 may be located anywhere on the device 10. In one embodiment, as shown in FIG. 2, the communication interface 18 is located within the handle 13 of the device 10. In one embodiment, the communication interface 18 is located on the frame 11.

The power source 20 powers the device 10. Namely, the power source 20 provides electrical power for the controller 12, the display 14, the input interface 16, the communication interface 18, the power source 20, the distance sensor 22, the force sensor 24, the rotating cylinder actuator 28, the rail system actuator 32, and the motor 36.

In one embodiment, the power source 20 is a wired connection that receives electricity from an electrical outlet. In one embodiment, as shown in FIGS. 1 and 2, the power source 20 is a battery. In one embodiment, the power source 20 is a battery that is removable from the device 10 and replaceable with another battery. In one embodiment, the power source 20 is rechargeable.

The distance sensor 22 measures a distance from the distance sensor 22 to a sliding component of the device 10. The sliding component may be any component of the device 10 that moves by the rail system 30, such as the rotating cylinder 26, the rotating cylinder actuator 28, the bit mount 34, a rail platform 72, a rail mount 74, or a threaded nut 78. The movement of the sliding components and the rail platform 72, the rail mount 74, and the threaded nut 78 will be discussed in further detail below.

In one embodiment, the distance sensor 22 measures a distance from the distance sensor 22 to the rotating cylinder 26. In one embodiment, the distance sensor 22 measures a distance from the distance sensor 22 to the rotating cylinder actuator 28. In one embodiment, the distance sensor 22 measures a distance from the distance sensor 22 to the bit mount 34. In one embodiment, the distance sensor 22 measures a distance from the distance sensor 22 to a rail platform 72, a rail mount 74, or a threaded nut 78 of the rail system 30. In one embodiment, the distance sensor 22 measures a distance from the distance sensor 22 to a housing or case that includes the rotating cylinder 26, the rotating cylinder actuator 28, the bit loader 33, the bit mount 34, the motor 36, and the torque limiter 38.

The distance sensor 22 may be any type of sensor that measures a distance between the distance sensor 22 and an object. For example, in one embodiment, the distance sensor 22 is a semiconductor device, such as a time-of-flight (ToF) sensor, that measures a distance based on a time difference between a transmission of a light signal (e.g., an infrared light signal) to an object and a reception of the light signal reflecting off of the object. A distance measurement obtained by the distance sensor 22 may be in the form of an electrical signal, such as an electrical current signal, a voltage signal, a resistance signal, etc.

The distance sensor 22 may be positioned anywhere on the device 10 in which the distance sensor 22 is able to obtain accurate distance measurements of a sliding component of the device 10. In one embodiment, as shown in FIGS. 1 and 2, the distance sensor 22 is positioned on the frame 11, adjacent to the rail system actuator 32.

As will be discussed in further detail below, distance measurements obtained by the distance sensor 22 are used during a drill process to measure a depth of a hole drilled by the device 10 into, for example, a bone.

The force sensor 24 measures an amount of force that is applied to a pressure component of the device 10. The pressure component may be any component of the device 10 that undergoes strain, stress, or pressure during a drill process or an implantation process, such as the bit mount 34 and a bit loaded into the bit mount 34.

In one embodiment, the force sensor 24 measures an amount of force that is applied to the bit mount 34. In one embodiment, the force sensor 24 measures an amount of force that is applied to a bit loaded into the bit mount 34.

The force sensor 24 may be any type of sensor that measures force, strain, or pressure. For example, in one embodiment, the force sensor 24 is a microelectromechanical pressure sensor. A force measurement obtained by the force sensor 24 may be in the form of an electrical signal, such as an electrical current signal, a voltage signal, a resistance signal, etc.

The force sensor 24 may be positioned anywhere on the device 10 in which the force sensor 24 is able to obtain accurate force measurements of a pressure component of the device 10. In one embodiment, as shown in FIGS. 1 and 2, the force sensor 24 is positioned on the rail system 30 and adjacent to the bit mount 34 such that the force sensor 24 measures an amount of force that is applied to a drill bit 46 loaded into the bit mount 34.

As will be discussed in further detail below, force measurements obtained by the force sensor 24 are used during a drill process to measure a depth of a hole drilled by the device 10 into, for example, a bone; and are used during an implantation process to determine when an implant, such as a screw, has made contact with an object, such as a bone or soft tissue.

The rotating cylinder 26 is positioned on the rail system 30. The rotating cylinder 26 is a housing that includes a plurality of chambers 48 for holding a plurality of different bits, such as drill bits and screw driver bits. For example, as shown in FIG. 2, one of the chambers 48 is holding a drill bit 50, and another one of the chambers 48 is holding a screw driver bit 52.

An uppermost chamber 56 of the chambers 48 is aligned with a through hole 58 that extends from the uppermost chamber 56 and through the motor 36 (more specifically a shaft extending through the motor 36) and the bit mount 34. As will be described in further detail below, when the uppermost chamber 56 is aligned with the through hole 58, a bit in the uppermost chamber 56 may be loaded from the uppermost chamber 56, through the through hole 58, and into the bit mount 34 to be used in a subsequent drill or implantation process. In one embodiment, a single chamber of the plurality of chambers 48 is aligned with the through hole 58 at a time.

As best shown in FIG. 1, the rotating cylinder 26 includes six chambers. The rotating cylinder 26, however, may include any number of chambers 48. In one embodiment, the rotating cylinder 26 includes at least two chambers. In one embodiment, the rotating cylinder 26 includes at least six chambers.

The rotating cylinder 26 may also hold any number of different types of bits. For example, a flat head screw driver bit, a Phillips screw driver bit, a hex screw driver bit, a brad point drill bit, and a multi-purpose drill bit of different sizes may be loaded into the chambers 48 of the rotating cylinder 26 at the same time. In one embodiment, he rotating cylinder 26 holds at least one drill bit and at least one screw driver bit.

As best shown in FIG. 1, the rotating cylinder 26 is cylindrical. However, other shapes are also possible. For example, the rotating cylinder 26 may instead have a cross section that is hexagonal, pentagonal, or square shaped.

Referring to FIG. 2, the rotating cylinder 26 is configured to rotate around an axis 54. By rotating around the axis 54, the rotating cylinder 26 is able to align each of the plurality of chambers 48 with the through hole 58 of the bit mount 34, one at a time. Stated differently, the rotating cylinder 26 is able to change the uppermost chamber 56 to be any one of the plurality of chambers 48. As a result, each of the bits in the plurality of chambers 48 may be loaded from the uppermost chamber 56, through the through hole 58, and into the bit mount 34. For example, referring to FIG. 2, the rotating cylinder 26 may be rotated to align the screw driver bit 52 with the through hole 58 to load the screw driver bit 52 into the bit mount 34. Similarly, the rotating cylinder 26 may be rotated to align the drill bit 50 with the through hole 58 to load the drill bit 50 into the bit mount 34.

The rotating cylinder actuator 28 is positioned on the rail system 30 and is coupled to the rotating cylinder 26. In one embodiment, as best shown in FIG. 2, the rotating cylinder actuator 28 is coupled to the rotating cylinder 26 by a gear shaft 60. The gear shaft 60 is inserted into a connector 62 of the rotating cylinder 26 such that the rotating cylinder 26 rotates as the rotating cylinder actuator 28 rotates the gear shaft 60. The rotating cylinder actuator 28 turns the rotating cylinder 26 to rotate around the axis 54.

In one embodiment, as best shown in FIG. 2, the rotating cylinder actuator 28 is positioned lateral to and aligned with the rotating cylinder 26.

The rotating cylinder actuator 28 may be any type of actuator that provides a rotating motion for the rotating cylinder 26. In one embodiment, the rotating cylinder actuator 28 is a rotary actuator.

The bit loader 33 is positioned on the rail system 30 and is coupled to the rotating cylinder 26. The bit loader 33 loads or inserts a bit in the uppermost chamber 56 into the bit mount 34. Namely, the bit loader 33 moves a bit in the uppermost chamber 56 from the uppermost chamber 56, through the through hole 58, and into the bit mount 34. Once the bit is inserted into the bit mount 34, the bit may then be used in a subsequent drill or implantation process.

The bit loader 33 also unloads or removes a bit from the bit mount 34 back into the uppermost chamber 56 when the uppermost chamber 56 is empty. In particular, the bit loader 33 moves a bit in the bit mount 34 from the bit mount 34, through the through hole 58, and into the uppermost chamber 56 when the uppermost chamber 56 is empty. Once the bit is placed back into the uppermost chamber 56, the rotating cylinder 26 may be rotated to change the uppermost chamber 56 to another one of the chambers 48 to load a different bit into the bit mount 34.

In one embodiment, as best shown in FIG. 2, the bit loader 33 is positioned on the connector 62.

The bit loader 33 may be any type of device that loads and unloads a bit between one of the plurality of chambers 48 and the bit mount 34. In one embodiment, the bit loader 33 is a mechanical device that utilizes an actuator to move a pin or arm, which in turn moves a bit between one of the plurality of chambers 48 and the bit mount 34.

The bit mount 34 is positioned on the rail system 30 and is coupled to the rotating cylinder 26. In one embodiment, as shown in FIGS. 1 and 2, the bit mount 34 and the rotating cylinder actuator 28 are positioned on opposite sides of the rotating cylinder 26. As discussed above, the bit mount 34 includes the through hole 58 that is aligned with the uppermost chamber 56 of the rotating cylinder 26. The bit mount 34 holds or clamps a bit to be used in a drill or implantation process. For example, as shown in FIGS. 1 and 2, the bit mount 34 secures the drill bit 46 during a drill process. In one embodiment, the bit mount 34 includes a clamp or a pin that holds a bit inserted into the bit mount 34 stationary. The bit mount 34 is sometimes referred to as a chuck.

Although the through hole 58 and the uppermost chamber 56 of the rotating cylinder 26 are discussed herein as being aligned with each other, the through hole 58 may be aligned with any one of the plurality of chambers 48 of the rotating cylinder 26. For example, the through hole 58 may be aligned with a lowermost chamber of the chambers 48 (i.e., the chamber holding the screw driver bit 52 in FIG. 2).

The motor 36 is positioned on the rail system 30 and is coupled to the bit mount 34. Referring to FIG. 2, the motor 36 turns or rotates the bit mount 34 around an axis 64. As the motor 36 rotates the bit mount 34, the bit loaded in the bit mount 34 also rotates around the axis 64. For example, referring to FIG. 2, as the motor 36 rotates the bit mount 34, the drill bit 46 rotates around the axis 64 to drill.

The motor 36 may be any type of motor that provides a rotating motion for the bit mount 34. In one embodiment, the motor 36 is a brushless motor. In one embodiment, the motor 36 is a brushed motor.

In one embodiment, the motor 36 and the bit mount 34 are separate components. For example, in one embodiment, the motor 36 is physically attached to the bit mount 34 to rotate the bit mount 34 around the axis 64.

In one embodiment, the motor 36 and the bit mount 34 are integrated together into a single device. For example, in one embodiment, the motor 36 is hollow shaft motor that includes a bit mount in the hollow shaft.

The torque limiter 38 is positioned on the rail system 30 and is positioned on the bit mount 34. The torque limiter 38 sets a maximum amount of torque that may be applied by the motor 36 to the bit mount 34 during operation. In one embodiment, as will be discussed in further detail below, the torque limiter 38 determines an endpoint of an implantation process to stop an implant from being inserted into a bone once a maximum torque is reached. This prevents possible damage to the bone and the motor 36. In one embodiment, the implantation process is stopped and reversed once translation has reached the depth measurement determined by the distance sensor 22.

In one embodiment, the torque limiter 38 is adjustable such that the maximum amount of torque applied by the motor 36 to the bit mount 34 may be changed.

The rail system 30 is positioned on an upper surface 65 of the frame 11. The rail system 30 is configured to move components of the device 10 that are positioned on the rail system 30, such as the force sensor 24, the rotating cylinder 26, the rotating cylinder actuator 28, the bit loader 33, the bit mount 34, the motor 36, and the torque limiter 38 along the upper surface 65 of the frame 11 in a first direction 66 and a second direction 68. These components are referred to herein as sliding components. As will be discussed in further detail below, the rail system 30 is configured to move the sliding components in the first direction 66 (i.e., left direction in FIG. 2) and/or the second direction 68 (i.e., right direction in FIG. 2) during, for example, a drill process and an implantation process.

The rail system 30 includes a track 70, a rail platform 72, a rail mount 74, a threaded rod 76, and a threaded nut 78.

The track 70 is positioned on the upper surface 65 of the frame 11. The track 70 is a track in which the rail platform 72 slides along in both the first direction 66 and the second direction 68. The track 70 also secures the rail platform 72 such that movement of the rail platform 72 in a direction transverse to the first direction 66 and the second direction 68 (e.g., a vertical direction in FIG. 2) is minimized.

The rail platform 72 is coupled to the track 70. As discussed above, the rail platform 72 is configured to move or slide along the track 70 in both the first direction 66 and the second direction 68.

The rail mount 74 is coupled to the rail platform 72. The rail mount 74 provides a platform for the sliding components. In one embodiment, as shown in FIGS. 1 and 2, the motor 36 is coupled to the rail mount 74; and the force sensor 24, the rotating cylinder 26, the rotating cylinder actuator 28, the bit loader 33, the bit mount 34, and the torque limiter 38 are positioned as discussed above.

The threaded rod 76 includes external threads that are mated with the threaded nut 78. In one embodiment, the external threads extend along at least most of the length of the threaded rod 76. The threaded rod 76 extends from a back plate 80 of the frame 11, through the rail mount 74 and the threaded nut 78, and to a front plate 82 of the frame 11. The threaded rod 76 is threaded and configured to rotate around an axis 84. In one embodiment, as best shown in FIG. 2, the threaded rod 76 is spaced from the rail mount 74 (i.e., does not physically contact the rail mount 74) and physically contacts the threaded nut 78.

The threaded nut 78 includes internal threads that are mated with the external threads of the threaded rod 76. As will be discussed in further detail below, because the threaded rod 76 and the threaded nut 78 are mated with each other, the external threads of the threaded rod 76 cause the threaded nut 78 to move parallel to axis 84 of rod when the threaded rod 76 is rotated by actuator 32. The threaded nut 78 may be coupled to the rail platform 72, the rail mount 74, or both of the rail platform 72 and the rail mount 74. As discussed above, the threaded nut 78 is mated with the threaded rod 76. In one embodiment, as shown in FIGS. 1 and 2, the threaded nut 78 is coupled to the rail mount 74. The threaded nut 78 is securely attached to the rail platform 72 and/or the rail mount 74 such that the rail platform 72 and/or the rail mount 74 moves along the track 70 with the threaded nut 78.

The rail system actuator 32 is coupled to the back plate 80 and the threaded rod 76. In one embodiment, as shown in FIG. 2, the rail system actuator 32 is coupled to the threaded rod 76 by a gear shaft 86. Namely, the gear shaft 86 is inserted into a connector 88 of the threaded rod 76 such that the threaded rod 76 rotates as the rail system actuator 32 rotates the gear shaft 86. In one embodiment, as best shown in FIG. 2, the rail system actuator 32 is positioned lateral to and aligned with the rail system 30. The rail system actuator 32 turns the threaded rod 76 to rotate around the axis 84.

The rail system actuator 32 may be any type of actuator that provides a rotating motion for the threaded rod 76. In one embodiment, the rail system actuator 32 is a rotary actuator.

In one embodiment, as shown in FIG. 2, the rotating cylinder actuator 28 and the rail system actuator 32 are two separate actuators. In one embodiment, a single actuator is used to provide functions of both the rotating cylinder actuator 28 and the rail system actuator 32. Namely, in one embodiment, a single actuator is used to turn the rotating cylinder 26 to rotate around the axis 54, and turn the threaded rod 76 to rotate around the axis 84.

The threaded rod 76, the threaded nut 78, and the rail system actuator 32, together, move or slide the rail platform 72 and the rail mount 74 along the track 70 in both the first direction 66 and the second direction 68. Namely, when the rail system actuator 32 rotates the threaded rod 76 in, for example, a clockwise direction, the threaded rod 76 rotates within the threaded nut 78 and causes the threaded nut 78 (with the rail platform 72 and the rail mount 74 attached) to move along the threaded rod 76 in, for example, the first direction 66. Conversely, when the rail system actuator 32 rotates the threaded rod 76 in, for example, a counter-clockwise direction, the threaded rod 76 rotates within the threaded nut 78 and causes the threaded nut 78 (with the rail platform 72 and the rail mount 74 attached) to move along the threaded rod 76 in, for example, the second direction 68. As the threaded nut 78, the rail platform 72, and the rail mount 74 move, so does the sliding components position on the rail mount 74 (e.g., the force sensor 24, the rotating cylinder 26, the rotating cylinder actuator 28, the bit loader 33, the bit mount 34, the motor 36, and the torque limiter 38 move along the upper surface 65 of the frame 11 in a first direction 66 and a second direction 68).

Figure 3:
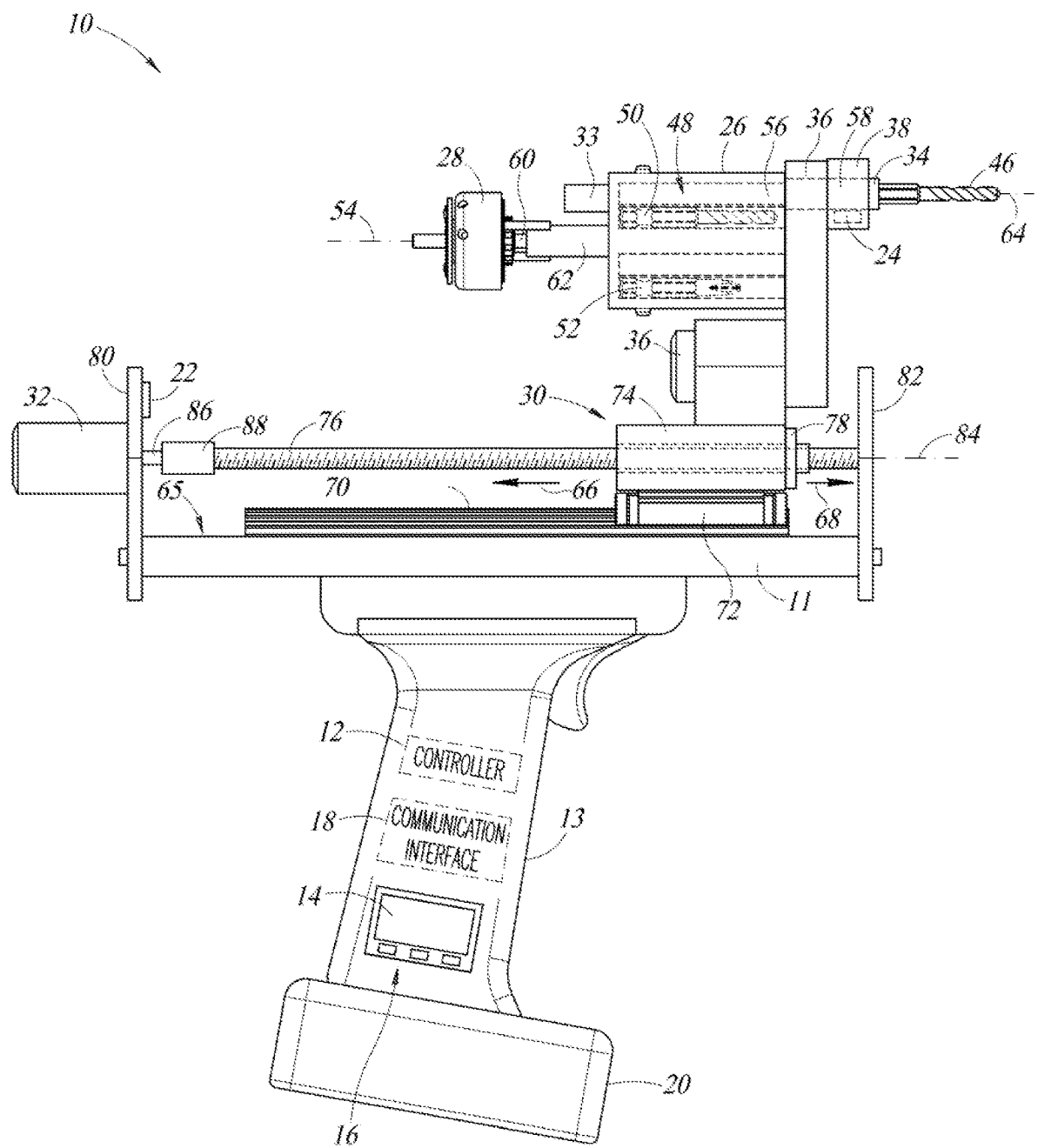
FIG. 3 is a side view of the device of FIG. 1 in another position.

FIG. 3 is a side view of the self-propelling device 10 in another position. In FIG. 3, the rail system actuator 32 rotates the threaded rod 76 within the threaded nut 78 and causes the threaded nut 78, the rail platform 72, and the rail mount 74 to move along the threaded rod 76 in the second direction 68. As a result, the rotating cylinder 26, the rotating cylinder actuator 28, the bit loader 33, the bit mount 34, the motor 36, and the torque limiter 38 are moved in the second direction 68.

In one embodiment, the rail system 30 does not include the rail mount 74. In this embodiment, the rail platform 72 provides a platform for the force sensor 24, the rotating cylinder 26, the rotating cylinder actuator 28, the bit loader 33, the bit mount 34, the motor 36, and the torque limiter 38. In this embodiment, the motor 36 is coupled to the rail platform 72, and the threaded nut 78 is coupled to the rail platform 72 such that the rail platform 72 moves along the track 70 with the threaded nut 78.

In one embodiment, the device 10 includes a camera such that remote observers outside of the surgical room may view a drill and implantation processes. In one embodiment, the camera is mounted adjacent to the bit mount 34. In one embodiment, the camera transfers data (e.g., image and/or video data) to an external device, such as a server, computer, tablet, mobile device (e.g., smart phone), and laptop, via the communication interface 18.

Figure 4:
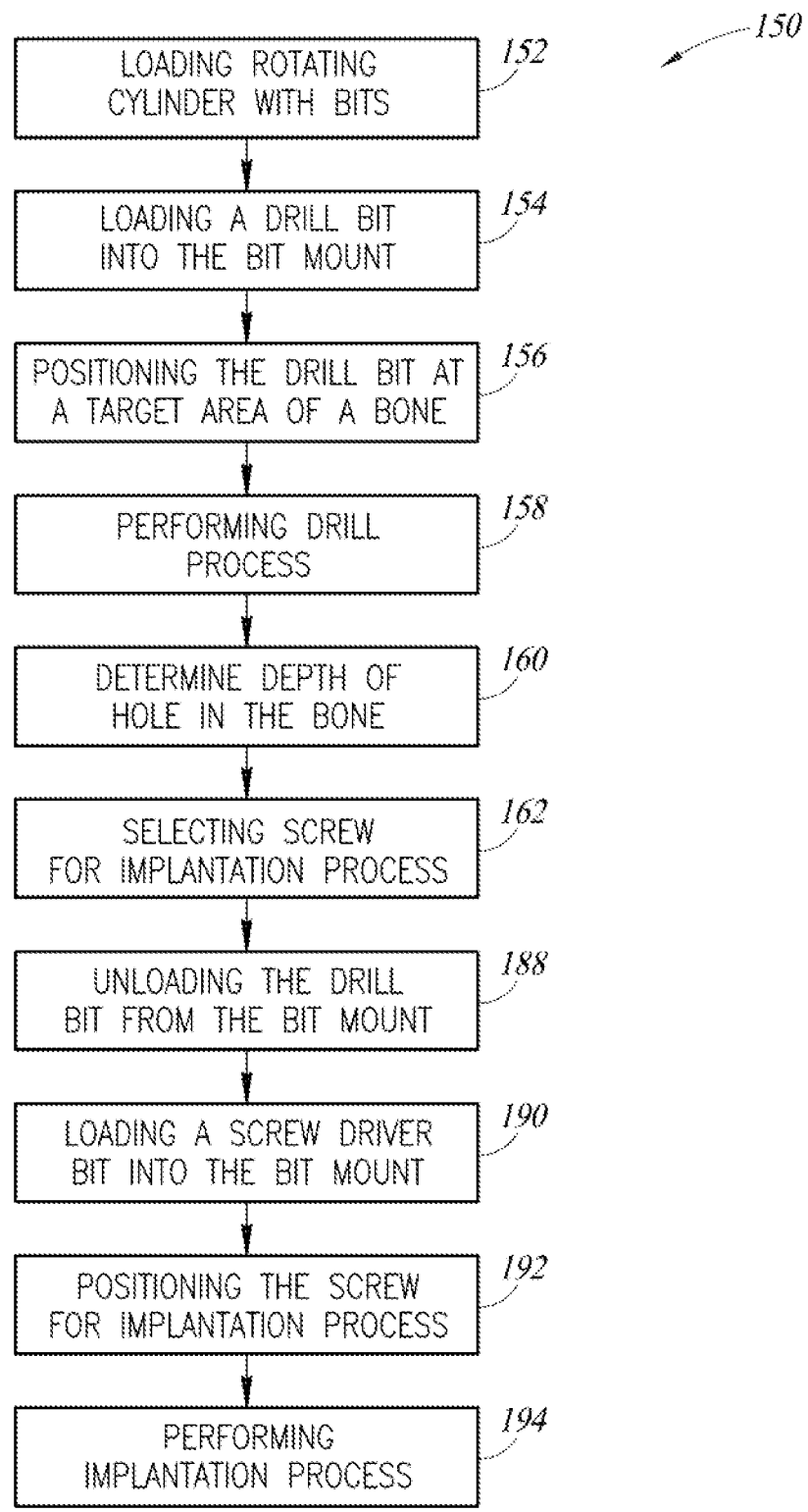
FIG. 4 is a block diagram of a method of operating the device of FIG. 1.

FIG. 4 is a block diagram of a method 150 of operating the device 10. The method 150 drills a hole into a bone, and subsequently inserts a screw into the hole in the bone. It is noted, however, the method 150 may be used to insert another type of implant, such as a pin, into another type of object.

In block 152, bits are loaded into the rotating cylinder 26. Namely, drill bits and screw driver bits are placed in the chambers 48 of the rotating cylinder 26. For example, as shown in FIGS. 1 and 2, the drill bit 50 and the screw driver bit 52 are inserted into separate chambers of the chambers 48. As previously discussed, the rotating cylinder 26 may include any number of chambers 48, and may be loaded with any number of different types of bits. In one embodiment, at least one drill bit and at least one screw driver bit are loaded into the rotating cylinder 26.

In block 154, a drill bit is loaded into the bit mount 34. The drill bit is selected from the rotating cylinder 26 and is inserted into the bit mount 34, where the drill bit is clamped. The controller 12 loads the drill bit into the bit mount 34 by instructing the rotating cylinder actuator 28 to rotate the rotating cylinder 26 until the uppermost chamber 56 is at a chamber that includes the desired drill bit (i.e., until the chamber that includes the desired drill bit is in the uppermost position), and instructing the bit loader 33 to load or insert the desired drill bit in the uppermost chamber 56 from the uppermost chamber 56, through the though hole 58, and into the bit mount 34.

In block 156, the drill bit is positioned at a target area of a bone. Stated differently, the user positions the device 10 such that a tip of the drill bit loaded in block 154 is in physical contact with a particular portion of the bone.

It is noted that once the device 10 is put into position in block 156, the device 10 remains stationary for the remainder of the method 150. Namely, the device 10 remains in the same position while blocks 158, 160, 162, 188, 190, 192, and 194 are performed.

In one embodiment, when in the manual mode, the device 10 can be removed and repositioned at the operator's discretion while blocks 156, 158, 160, 162, 192 and 194 are performed.

In block 158, a drill process is performed. The drill process drills a hole into the target area. The controller 12 performs the drill process by instructing the motor 36 to turn on and rotate the bit mount 34 and the drill bit around the axis 64. While the motor 36 is turned on, the controller 12 instructs the rail system actuator 32 to turn on and rotate the threaded rod 76 to move the threaded nut 78 in the second direction 68. As discussed above, as threaded nut 78 moves along the threaded rod 76, so do the sliding components (the rotating cylinder 26, the rotating cylinder actuator 28, the bit loader 33, the bit mount 34, the motor 36, and the torque limiter 38, rail platform 72, and the rail mount 74). As a result, the drill bit is simultaneously rotated by the motor 36 and moved in the second direction 68 by the rail system actuator 32; and, thus, drills into the target area.

Once a desired depth of the hole is reached, the drill bit is retracted from the bone. The determination of the depth of the hole is described with respect to block 160. The controller 12 retracts the drill bit by instructing the rail system actuator 32 to turn on and rotate the threaded rod 76 to move the threaded nut 78 in the first direction 66. As discussed above, as threaded nut 78 moves along the threaded rod 76, so do the sliding components (the rotating cylinder 26, the rotating cylinder actuator 28, the bit loader 33, the bit mount 34, the motor 36, and the torque limiter 38, rail platform 72, and the rail mount 74).

It is noted that the device 10 itself remains stationary during the drill process in block 158, including the retraction of the drill bit. The drilling is performed by the drill bit being simultaneously rotated by the motor 36 and moved in the second direction 68 by the rail system actuator 32. The user does not apply physical force to push the device 10 to drill the drill bit into the bone. As a result, the user will not suffer from fatigue after drilling several holes.

In block 160, a depth of the hole in the bone is determined. Namely, the depth of the resulting hole of the drill process in block 158 is measured. The controller 12 determines the depth of the hole as a distance a sliding component of the device 10 (e.g., the rotating cylinder 26, the rotating cylinder actuator 28, the bit mount 34, the rail platform 72, the rail mount 74, or the threaded nut 78) has moved during the drill process in block 158 from a starting position to an ending position. The distance the sliding component of the device 10 has moved during the drill process is determined based on distance measurements by the distance sensor 22.

In one embodiment, the starting position is a position in which the drill bit makes first physical contact with the bone on a first side, and the ending position is a position in which the user has ended the drill process. In this embodiment, the starting position is determined based on force measurements by the force sensor 24. In particular, the controller 12 sets the starting position as the position of, for example, the rail platform 72 at a time of a first force measurement being greater than a first predetermined threshold. The ending position is determined based on an action taken by the user to end the drill process. In particular, the controller 12 sets the ending position as the position of the rail platform 72 at a time of the user, for example, pressing a button on the input interface 16 or releasing the trigger 17 to end the drill process. The depth of the hole in the bone is then determined as the distance the rail platform 72 has moved during the drill process from the starting position to the ending position.

In one embodiment, the starting position is a position in which the drill bit makes first physical contact with the bone on a first side, and the ending position is a position in which the drill bit exits the bone on a second side that is opposite to the first side. In this embodiment, the starting position and the ending position are determined based on force measurements by the force sensor 24. The controller 12 sets the starting position as the position of, for example, the rail platform 72 at a time of a first force measurement being greater than a first predetermined threshold; and sets the ending position as the position of the rail platform 72 at a time of a second force measurement, which is obtained subsequent to the first force measurement, being less than a second predetermined threshold. The depth of the hole in the bone is then determined as the distance the rail platform 72 has moved during the drill process from the starting position to the ending position.

In one embodiment the drill process is stopped once the ending position is reached. Thus, the possibility of drilling the hole too deep and injuring the patient by, for example, penetrating soft tissue is minimized.

Figure 5:
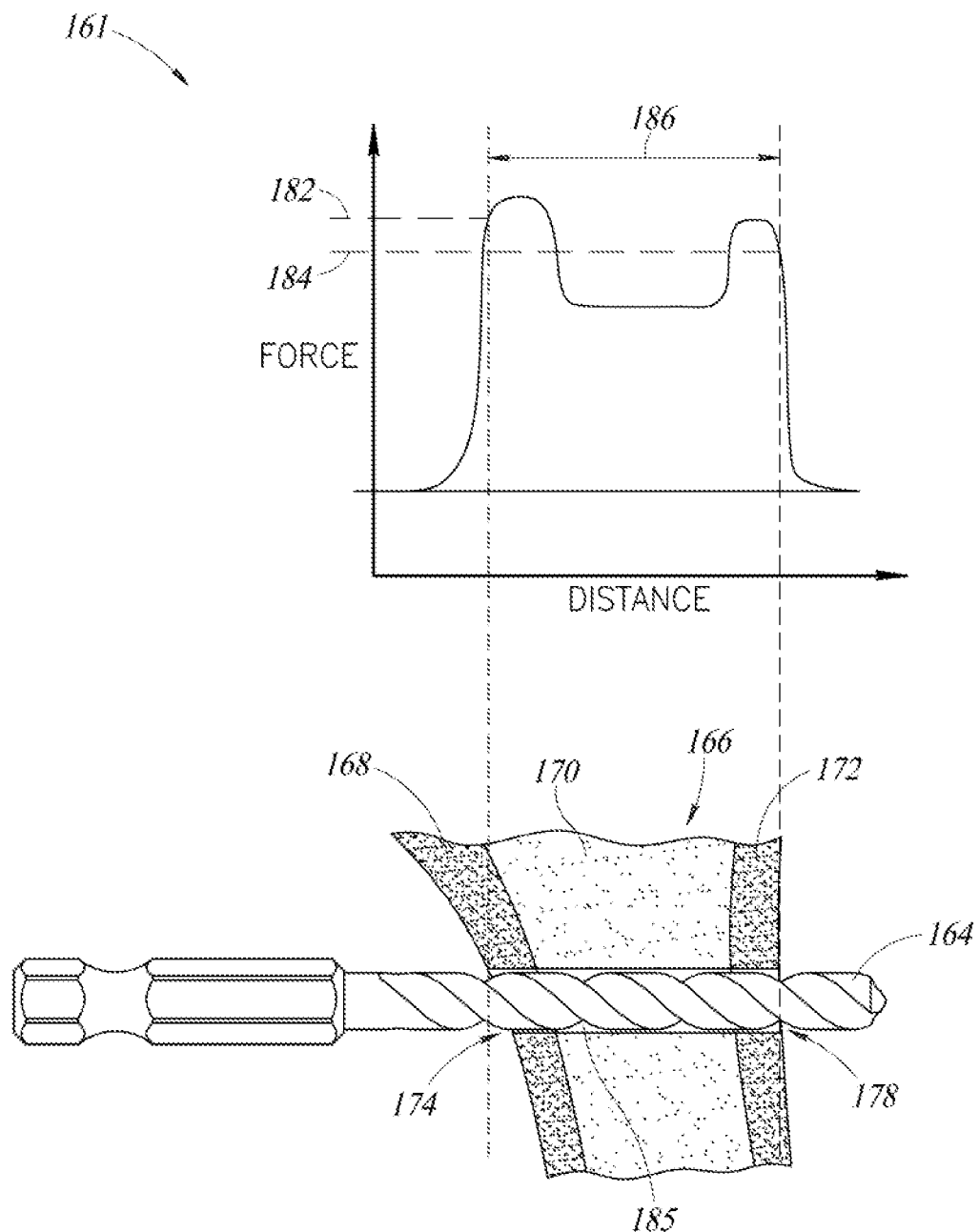
FIG. 5 is a diagram showing distance and force measurements during a drill process according to an embodiment of the present disclosure.

FIG. 5 illustrates an example of how a depth of a hole drilled into a bone is measured in block 160. In the example shown in FIG. 5, the starting position is a position in which the drill bit makes first physical contact with the bone on a first side and the ending position is a position in which the drill bit exits the bone on a second side that is opposite to the first side.

FIG. 5 is a diagram showing distance and force measurements during a drill process according to an embodiment of the present disclosure. Graph 161 shows distance measurements versus force measurements, when a drill bit 164 is drilled through a bone 166. The bone 166 includes a near cortical 168, an intramedullary cavity 170, and a far cortical 172.

As can be seen from the graph 161, as the near cortical 168 and the far cortical 172 are harder than the intramedullary cavity 170, force measurements increases as the drill bit 164 goes through the near cortical 168, decreases as the drill bit 164 goes through the intramedullary cavity 170, increases again as the drill bit 164 goes through the far cortical 172, and decreases again as the drill bit 164 exits the far cortical 172 into the soft tissue.

The starting position is a first position 174 where the drill bit 164 makes first physical contact with the near cortical 168 of the bone 166. The starting position is determined as a position of a sliding component (e.g., the rotating cylinder 26, the rotating cylinder actuator 28, the bit mount 34, the rail platform 72, the rail mount 74, or the threaded nut 78) at a time of the force being equal to or greater than a first predetermined threshold 182.

Similarly, the ending position is a second position 178 where the drill bit 164 exits the far cortical 172 of the bone 166. The ending position is determined as a position of the sliding component at a time of the force being equal to or less than a second predetermined threshold 184.

Once the starting position (the first position 174) and the ending position (the second position 178) are determined, the depth of a hole 185 drilled into the bone 166 is determined as a distance 186.

It is noted that, although the first predetermined threshold 182 and the second predetermined threshold 184 are shown to be different than each other, the first predetermined threshold 182 and the second predetermined threshold 184 may also be set to the same value.

In one embodiment, a current depth of the resulting hole of the drill process in block 158 is measured concurrently with the drill process and in real time. In this embodiment, the starting position is a position in which the drill bit makes first physical contact with the bone on a first side, and is determined based on force measurements by the force sensor 24. In particular, the controller 12 sets the starting position as the position of, for example, the rail platform 72 at a time of a first force measurement being greater than a first predetermined threshold. The current depth of the hole in the bone is then determined as the distance between the starting position and a current position of the rail platform 72. In one embodiment, the current depth of the hole is displayed on the display 14. As such, the user may easily determine whether or not a desired depth of the hole has been reached, and end the drill process by, for example, pressing a button on the input interface 16 or releasing the trigger 17 in response to the desired depth being reached. Thus, the possibility of drilling the hole too deep and injuring the patient by, for example, penetrating soft tissue is minimized.

The device 10 is able to obtain an accurate depth measurement of the hole in block 160 because the depth of the hole is determined concurrently with the drill process and is determined based on distance measurements by the distance sensor 22 and force measurements by the force sensor 24. As a result, the possibility of the user inserting a screw with the wrong length in a subsequent implantation process may be minimized, and the amount of wasted hardware and total costs may be reduced. Further, the number of radiographs to verify the depth of the hole may be reduced; thus, avoid exposing the patient, surgeon, and staff to harmful radiation from the radiographs.

In addition, because the depth of the hole is determined concurrently with the drill process and is determined based on distance measurements by the distance sensor 22 and force measurements by the force sensor 24, the device 10 is able to remain stationary during blocks 156, 158, and 160. That is the user does not have to repeatedly drill the hole, remove the device 10, and measure the depth of the hole until the hole reaches a desired depth. As a result, the overall time to complete the method 150 is much shorter than other drill and implantation processes.

Returning to the method 150, in block 162, a screw for a subsequent implantation process is selected.

In one embodiment, the controller 12 selects the screw based on the drill bit used in blocks 154, 156, and 158. For example, the diameter of the screw is selected based on the drill bit used in blocks 154, 156, and 158.

In one embodiment, the controller 12 selects the screw based on the depth determined in block 160. For example, in one embodiment, a screw having a length that is equal to or greater than the depth determined in block 160 is selected.

In one embodiment, the controller 12 selects the screw based on the target area. For example, in one embodiment, the controller 12 selects the screw based on whether the screw is inserted directly into bone, through a plate, or either unicortical or bicortical.

In block 188, the drill bit is unloaded from the bit mount 34. In particular, the drill bit that was loaded into the bit mount 34 in block 154 is removed from the bit mount 34 and placed back into the rotating cylinder 26. The controller 12 unloads the drill bit from the bit mount 34 by instructing the rotating cylinder actuator 28 to rotate the rotating cylinder 26 until the uppermost chamber 56 is an empty chamber, and instructing the bit loader 33 to remove the drill bit from bit mount 34 and place the drill bit in the uppermost chamber 56. In one embodiment, the bit mount 34 utilizes an actuator to move a pin or arm to remove the drill bit from the bit mount 34.

Although block 188 is shown to be subsequent to block 162, block 188 may be performed prior to or concurrently with block 162.

In block 190, a screw driver bit is loaded into the bit mount 34. The screw driver bit is selected from the rotating cylinder 26 and is inserted into the bit mount 34, where the screw driver bit is clamped. The controller 12 loads the screw driver bit into the bit mount 34 by instructing the rotating cylinder actuator 28 to rotate the rotating cylinder 26 until the uppermost chamber 56 is a chamber that includes the desired screw driver bit, and instructing the bit loader 33 to load or insert the desired screw driver bit in the uppermost chamber 56 from the uppermost chamber 56, through the though hole 58, and into the bit mount 34.

In one embodiment, the screw driver bit that is loaded into the bit mount 34 is selected based on the drill bit used in blocks 154, 156, and 158. For example, in one embodiment, a screw driver bit having a diameter that is equal to or less than a diameter of the drill bit used in blocks 154, 156, and 158 is selected.

In one embodiment, the screw driver bit that is loaded into the bit mount 34 is selected based on the screw selected in block 162. For example, in one embodiment, if a screw having a hexgonal head is selected in block 162, a hexagonal head screw driver bit is loaded into the bit mount 34.

In block 192, the screw selected in block 162 is positioned for the implantation process. Namely, the screw is positioned in front of and aligned with the screw driver bit loaded in block 190.

In one embodiment, the screw selected in block 162 is positioned manually by the user. For example, the user physically places the screw in front of and aligned with the screw driver bit loaded in block 190.

In one embodiment, one or more screws are positioned in the chambers 48 of the rotating cylinder 26. In this embodiment, subsequent to block 188 and prior to block 190, the screw selected in block 162 is selected from one of the chambers 48 of the rotating cylinder 26 and is inserted into the bit mount 34. The controller 12 loads the screw into the bit mount 34 by instructing the rotating cylinder actuator 28 to rotate the rotating cylinder 26 until the uppermost chamber 56 is at a chamber that includes the screw selected in block 162 (i.e., until the chamber that includes the screw selected in block 162 is in the uppermost position), and instructing the bit loader 33 to load or insert the desired screw in the uppermost chamber 56 from the uppermost chamber 56, through the though hole 58, and into the bit mount 34. Subsequently, a screw driver bit is loaded into the bit mount 34 as described with respect to block 190.

In one embodiment, the screw selected in block 162 is positioned by a screw cartridge that is attached to the device 10 and dispenses the screw in front of and aligned with the screw driver bit loaded in block 190.

Figure 6:
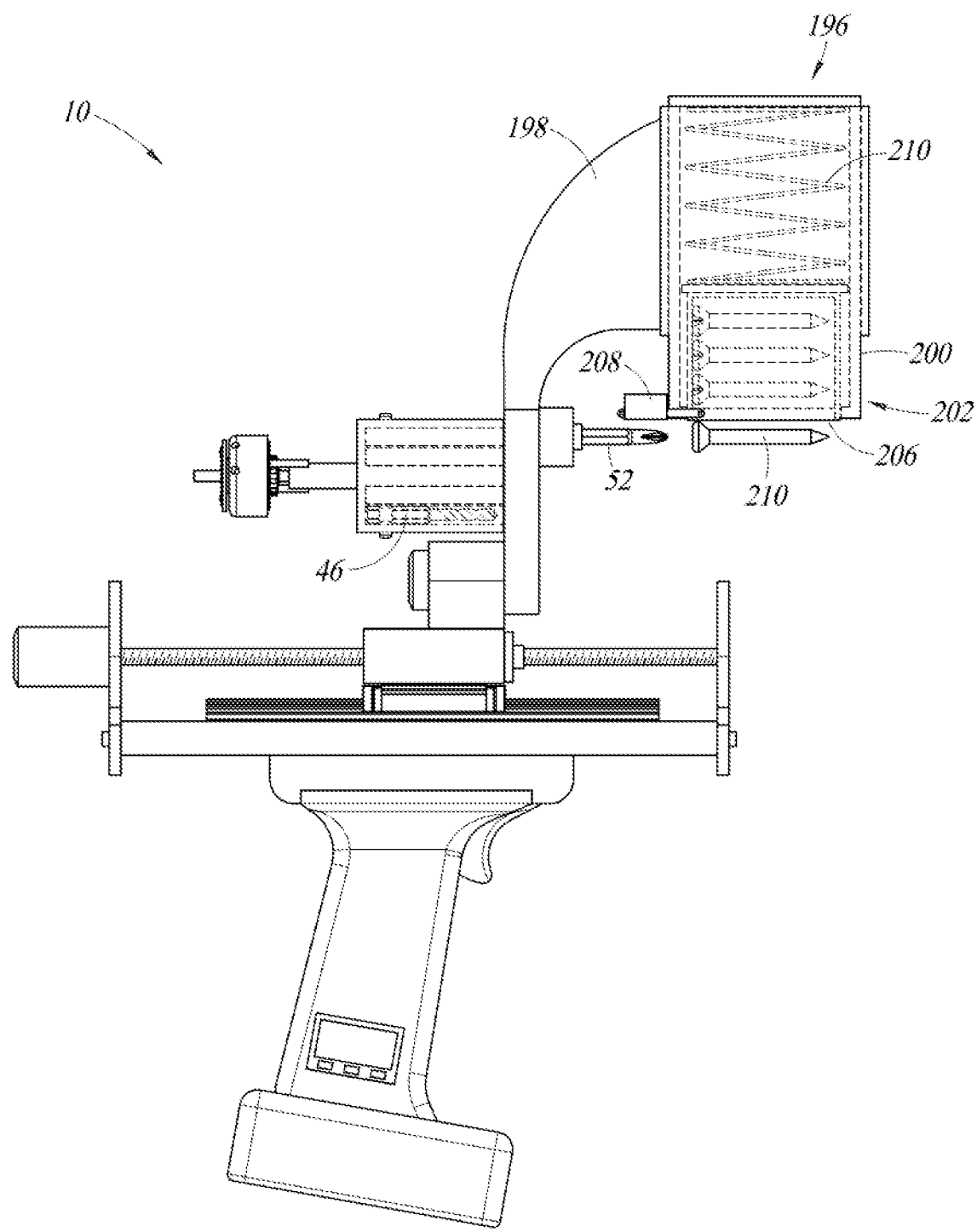
FIG. 6 is a side view of the device of FIG. 1 and a screw cartridge according to an embodiment of the present disclosure.

FIG. 6 illustrates an example of a screw cartridge for dispensing and positioning the screw selected in block 162 in front of and aligned with the screw driver bit loaded in block 190.

FIG. 6 is a side view of the device 10 and a screw cartridge 196 according to an embodiment of the present disclosure. In contrast to the device 10 shown in FIGS. 1 and 2, the screw driver bit 52 is loaded into the bit mount 34 and the drill bit 46 is placed back into a chamber of the rotating cylinder 26.

The screw cartridge 196 includes a screw cartridge mount 198, a body 200, screws 202, a door 206, a door actuator 208, and a spring 210.

The screw cartridge mount 198 couples the screw cartridge 196 to the device 10. The screw cartridge 196 is positioned such that a dispensed screw 210 of the screws 202 is positioned in front of and aligned with the screw driver bit 52.

The body 200 houses the screws 202. The body 200 may hold any number of screws. In one embodiment, each of the screws 202 is a screw selected in block 162.

The door 206 opens and closes to dispense one of the screws 202. When the door 206 is in an open position one of the screws 202 is pushed downward by the spring 210, and dispensed from the body 200 and in front of the screw driver bit 52. When the door 206 is in a closed position none of the screws 202 are dispensed from the body 200. The door 206 is in the closed position in FIG. 6.

The door actuator 208 is coupled to the door 206. The door actuator 208 moves the door 206 between the open position and the closed position. The door actuator 208 may be any type of actuator that moves the door 206 between the open position and the closed position. For example, the door actuator 28 may be a linear actuator or a rotary actuator.

The spring 210 is inserted into the body 200 and applies a downward force on the screws 202. As a result, a screw of the screws 202 is dispensed from the body 200 when the door 206 is in the open position.

In one embodiment, the screw cartridge 196 is removable from the device 10. Namely, the screw cartridge 196 may be easily attached and detached from the device 10. In one embodiment, the screw cartridge 196 is attached to the device 10 in block 192, and then detached once the screw selected in block 162 has been dispensed for the implantation process.

Figure 7:
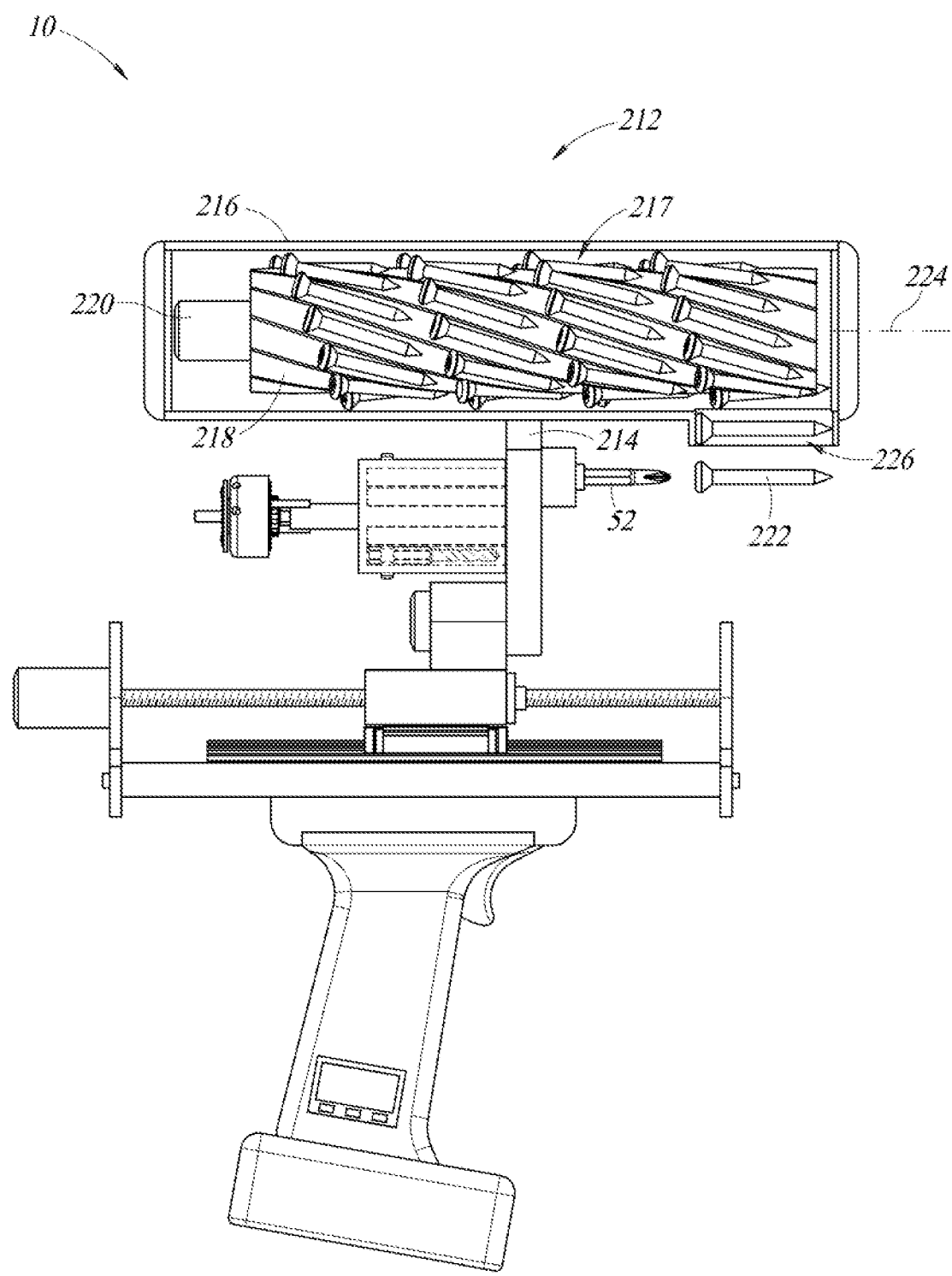
FIG. 7 is a helical feed system according to an embodiment of the present disclosure.

In one embodiment, the screw selected in block 162 is positioned by a helical feed system. In this embodiment, the helical feed rotates to dispense and position the screw selected in block 162 in front of and aligned with the screw driver bit loaded in block 190. FIG. 7 is a helical feed system 212 according to an embodiment of the present disclosure.

The helical feed system 212 includes helical feed system mount 214, a body 216, screws 217, a rotating barrel 218, and a rotating barrel actuator 220.

The helical feed system mount 214 couples the helical feed system 212 to the device 10. The helical feed system 212 is positioned such that a dispensed screw 222 of the screws 217 is positioned in front of and aligned with the screw driver bit 52.

The body 216 houses the screws 217. The body 216 may hold any number of screws. In one embodiment, each of the screws 217 is a screw selected in block 162.

The rotating barrel 218 rotates around an axis 224. By rotating around the axis 224, one of the screws 217 is dispensed from the body 216. Namely, as the rotating barrel 28 rotates, a screw nearest to an opening 226 in the body 216 is pushed out of the opening 226 by the remaining screws in the body 216.

The rotating barrel actuator 220 is coupled to the rotating barrel 218. The rotating barrel actuator 220 turns the rotating barrel 218 to rotate around the axis 224. The rotating barrel actuator 220 may be any type of actuator that provides a rotating motion for the rotating barrel 218. In one embodiment, the rotating barrel actuator 220 is a rotary actuator.

Returning to the method 150, in block 194, an implantation process is performed to screw the screw selected in block 162 into the hole drilled by the drill process in block 158. The controller 12 performs the implantation process by instructing the motor 36 to turn on and rotate the bit mount 34 and the screw driver bit loaded in block 190 around the axis 64. While the motor 36 is turned on, the controller 12 instructs the rail system actuator 32 to turn on and rotate the threaded rod 76 to move the threaded nut 78 in the second direction 68. As discussed above, as threaded nut 78 moves along the threaded rod 76, so do the sliding components (the rotating cylinder 26, the rotating cylinder actuator 28, the bit loader 33, the bit mount 34, the motor 36, and the torque limiter 38, rail platform 72, and the rail mount 74). As a result, the screw driver bit is simultaneously rotated by the motor 36 and moved in the second direction 68 by the rail system actuator 32; and, thus, screws the screw selected in block 162 into the hole.

Once the screw is screwed into the hole to a desired depth, the screw driver bit is retracted. Namely, the controller 12 instructs the rail system actuator 32 to turn on and rotate the threaded rod 76 to move the threaded nut 78 in the first direction 66. As discussed above, as threaded nut 78 moves along the threaded rod 76, so do the sliding components (the rotating cylinder 26, the rotating cylinder actuator 28, the bit loader 33, the bit mount 34, the motor 36, and the torque limiter 38, rail platform 72, and the rail mount 74).

In one embodiment, the controller 12 determines the screw has reached a desired depth based on force measurements obtained by the force sensor 24. The force measurements are used to determine when the screw has made contact with an object, such as a bone or soft tissue. For example, the controller 12 may determine that the screw has made contact with the bone when a force measurement is greater than a first predetermined threshold, and determine the screw has made contact with soft tissue when a force measurement is greater than a second predetermined threshold lower than the first predetermined threshold. In response to the controller 12 determining the screw has made contact with the object, the controller 12 stops the implantation process and begins retracting the screw driver bit. As a result, damage to the bone and the soft tissue may be prevented.

In one embodiment, the controller 12 determines the screw has reached a desired depth using the torque limiter 38. As discussed above, the torque limiter 38 sets an amount of torque that may be applied by the motor 36 to the bit mount 34 during operation. When the maximum amount of torque is reached, the controller 12 stops the implantation process and begins retracting the screw driver bit. As a result, damage to the bone and the motor 36 may be prevented.

In one embodiment, the controller 12 determines the screw has reached a desired depth based on the depth determined in block 160 and a distance a sliding component of the device 10 (e.g., the rotating cylinder 26, the rotating cylinder actuator 28, the bit mount 34, the rail platform 72, the rail mount 74, or the threaded nut 78) has moved during the implantation process in block 194. The distance the sliding component of the device 10 has moved during the drill process is determined based on distance measurements by the distance sensor 22. For example, in one embodiment, the controller 12 determines that the screw has reached a desired depth in response to a sliding component moving a distance equal to the depth determined in block 160.

It is noted that the device 10, itself, remains stationary during the implantation process, including the retraction of the screw driver bit. The screwing is performed by the screw driver bit being simultaneously rotated by the motor 36 and moved in the second direction 68 by the rail system actuator 32. The user does not have to apply physical force to push the device 10 to screw the screw selected in block 162 into the hole. As a result, the user will not suffer from fatigue after drilling several holes. In addition, the possibility of the screw being inserted into the hole at the wrong angle and/or alignment is minimized as the device 10 remains stationary from block 156.

Figure 8:
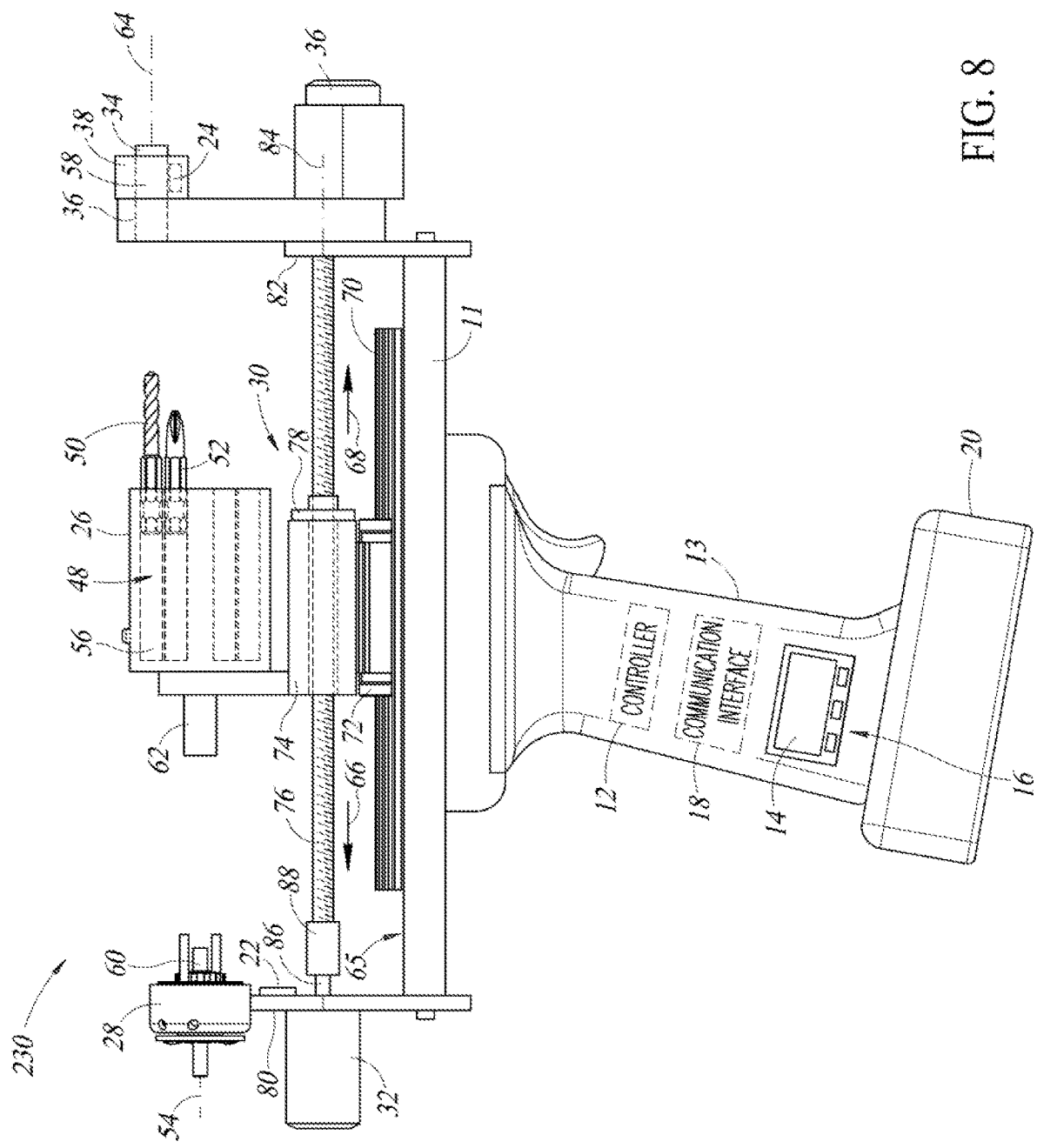
FIG. 8 is a side view of a self-propelling device according to another embodiment of the present disclosure.

FIG. 8 is a side view of a self-propelling device 230 according to another embodiment of the present disclosure. The device 230 is similar to the device 10, except that one or more of the rotating cylinder actuator 28, the bit mount 34, the motor 36, and/or the torque limiter 38 are coupled to the frame 11 instead of the rail platform 72. As a result, the rotating cylinder actuator 28, the bit mount 34, the motor 36, and/or the torque limiter 38 remain stationary, while the rotating cylinder 26 is moved in the first direction 66 and the second direction 68 via the rail system 30.

In one embodiment, as shown in FIG. 8, the rotating cylinder actuator 28 is coupled to the back plate 80. In this embodiment, when the rotating cylinder 26 should be rotated, the rotating cylinder 26 is moved in the first direction 66 via the rail system 30 until the gear shaft 60 is inserted into the connector 62 of the rotating cylinder 26 such that the rotating cylinder 26 rotates as the rotating cylinder actuator 28 rotates the gear shaft 60. Once the rotating cylinder 26 has been rotated to a desired position, the rotating cylinder 26 may then be moved in the second direction to perform a drill process or an implantation process as described above.

In one embodiment, as shown in FIG. 8, the bit mount 34, the motor 36, and the torque limiter 38 are coupled to front plate 82. In this embodiment, bits in the chambers 48 extend outside of the rotating cylinder 26. For example, as shown in FIG. 8, the drill bit 50 and the screw driver bit 52 extend outside of the chambers 48 and in front of the rotating cylinder 26. Because the bits extend outside of the rotating cylinder 26, a bit in the uppermost chamber 56 is loaded from the uppermost chamber 56, through the through hole 58, and into the bit mount 34 by simply moving the rotating cylinder 26 in the second direction 68 via the rail system 30. Thus, the bit loader 33 may be removed in this embodiment. For example, the drill bit 50 may be loaded into the bit mount 34 by moving the rotating cylinder 26 in the second direction 68 until the drill bit 50 is positioned in the through hole 58. It is noted the motor 36 shown in FIG. 8 is modified from the motor 36 shown, for example, in FIGS. 1 and 2. In particular, the motor 36 shown in FIG. 8 reduced in size such that the bits besides the bit in the uppermost chamber 56 (e.g., the screw driver bit 52 in FIG. 8) do not physically contact the motor 36 when the rotating cylinder 26 is moved in the second direction 68.

The various embodiments described above provide a self-propelling surgical device and method for using the same. The device is configured to drill a hole into an object, such as a bone; determine a depth of the hole; select an implant, such as a screw to be inserted into the hole; and insert the implant into the hole. The device is able to perform the drilling and the implantation without applying a physical force to the device. Further, the user may leave the device in a stationary position during the drilling and the implantation.

Although the various embodiment described above utilize the device 10 for surgical applications, the device 10 may be used for other applications as well. For example, the device 10 may be used for construction applications, home improvement applications, and various other types of applications.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A medical device, comprising:
a handle;
a frame coupled to the handle, the frame including a back plate and a front plate, the back plate and the front plate being positioned on opposite sides of the frame;
a track on the frame;
a mount on the track;
a threaded nut on the mount;
a threaded rod that extends through the mount and the threaded nut;
a first actuator on the back plate, the first actuator configured to rotate the threaded rod and move the mount along the track while the frame and the track remain in fixed positions with respect to the handle;
a housing on the mount, the housing including a plurality of chambers;

a second actuator on the housing, the second actuator configured to rotate the housing;
a bit mount on the housing; and
a motor on the mount, the motor configured to rotate the bit mount, wherein the housing, the second actuator, the bit mount, and the motor are configured to move with the mount along the track while the frame and the track remain in fixed positions with respect to the handle.

2. The medical device of claim 1, further comprising:
a drill bit in one of the plurality of chambers; and
a screw driver bit in one of the plurality of chambers.

3. The medical device of claim 1, further comprising:
a distance sensor configured to measure a distance between the distance sensor and the mount or a distance between the distance sensor and the housing.

4. The medical device of claim 3, further comprising:
a force sensor configured to measure a force applied to a bit in the bit mount.

5. The device of claim 1, further comprising:
a screw dispenser configured to dispense a screw in front of and aligned with a bit mounted in the bit mount, the screw cartridge being coupled to the mount such that the screw cartridge is configured to move with the mount along the track while the frame and the track remain in fixed positions with respect to the handle.

6. A device, comprising:
a handle;
a frame coupled to the handle;
a track on the frame;
a platform on the track and configured to move along the tack while the frame and the track remain in fixed positions with respect to the handle;
a housing affixed to the platform and configured to rotate while affixed to the platform, tae housing including a plurality of chambers configured to house a plurality of bits, the housing configured to move with the platform along the track while the frame and the track remain in fixed positions with respect to the handle; and
a bit mount configured to receive one of the plurality of bits.

7. The device of claim 6, further comprising:
a threaded nut on the platform; and
a threaded rod that extends through the platform and the threaded nut.

8. The device of claim 6, further comprising:
an actuator on the frame and configured to move the platform along the track.

9. The device of claim 6, further comprising:
an actuator attached to the housing and configured to rotate the housing.

10. The device of claim 6, further comprising:
a motor attached to the bit mount and configured to rotate the bit mount.

11. The device of claim 6, further comprising:
a distance sensor configured to measure a distance between the distance sensor and the platform or a distance between the distance sensor and the housing.

12. The device of claim 6, further comprising:
a force sensor configured measure a force applied to a bit in the bit mount.

13. The device of claim 6, further comprising:
a controller configured to control the device to perform a drill process and an implantation process;
a communication interface configured to receive parameters for the drill process and the implantation process; and
a display configured to display the parameters.

14. The device of claim 6, further comprising:
a first actuator configured to move the platform along the track while the frame and the track remain in fixed positions with respect to the handle;
a second actuator configured to rotate the housing; and
a motor configured to rotate the bit mount,
the housing, the bit mount, the second actuator, and the motor being positioned on the platform such that the housing, the bit mount, the second actuator, and the motor move with the platform along the track while the frame and the track remain in fixed positions with respect to the handle.

15. The device of claim 6 wherein
the frame includes a back plate and a front plate,
the back plate and the front plate are positioned on opposite sides of the frame,
the track is positioned between the back plate and the front plate, and
the device further includes:
  a first actuator on the back plate, the first actuator configured to move the platform along the track while the frame and the track remain in fixed positions with respect to the handle;
  a second actuator on the platform, the second actuator configured to rotate the housing; and
  a motor on the front plate, the motor configured to rotate the bit mount.

16. A device, comprising:
a handle;
a frame coupled to the handle, the frame including a back plate and a front plate, the back plate and the front plate being positioned on opposite sides of the frame;
a track on the frame, the track being positioned between the back plate and the front plate;
a mount configured to move along the track, from the back plate towards the front plate, and from the front plate towards the back plate;
a threaded nut coupled to the mount;
a threaded rod extending from the back plate, through the mount and the threaded nut, and to the front plate;
a first actuator coupled to the back plate, the first actuator configured to rotate the threaded rod and move the mount along the track;
a housing coupled to the mount, the housing including a plurality of chambers configured to house a plurality of bits, the housing configured to move with the mount along the track;
a second actuator coupled to the back plate, the second actuator configured to rotate the housing;
a bit mount coupled to the front plate, the bit mount configured to receive a bit of the plurality of bits; and
a motor coupled to the front plate, the motor configured to rotate the bit mount.

17. The device of claim 16, further comprising:
an input interface on the handle.

18. The device of claim 16, further comprising:
a distance sensor coupled to the back plate, the distance sensor configured to measure a distance between the distance sensor and the mount or a distance between the distance sensor and the housing; and
a force sensor coupled to the bit mount, the force sensor configured to measure a force applied to a bit in the bit mount.

19. A device, comprising:
a handle;
a frame coupled to the handle;
a track on the frame;

a platform on the track and configured to move along the track while the frame and the track remain in fixed positions with respect to the handle;
a housing on the platform and configured to rotate, the housing including a plurality of chambers configured to house a plurality of bits, the housing configured to move with the platform along the track while the frame and the track remain in fixed positions with respect to the handle;
a bit mount configured to receive one of the plurality of bits; and
an actuator attached to the housing and configured to rotate the housing.

20. The device of claim 19, further comprising:
a motor attached to the bit mount and configured to rotate the bit mount.

\* \* \* \* \*

UNITED STATES PATENT AND TRADEMARK OFFICE
CERTIFICATE OF CORRECTION

PATENT NO. : 10,820,911 B2
APPLICATION NO. : 16/514896
DATED : November 3, 2020
INVENTOR(S) : Allan Michael Delman et al.

It is certified that error appears in the above-identified patent and that said Letters Patent is hereby corrected as shown below:

In the Claims

<u>Column 19, Line 31, Claim 6:</u>
"tack" should read: --track--.

<u>Column 19, Line 34, Claim 6:</u>
"tae" should read: --the--.

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*